(12) United States Patent
Bostley et al.

(10) Patent No.: US 9,810,001 B2
(45) Date of Patent: Nov. 7, 2017

(54) LOCKABLE RETAINER ASSEMBLY

(71) Applicant: RC Imaging, Inc., Hilton, NY (US)

(72) Inventors: Eric Bostley, Hilton, NY (US); Brian Giardino, Rochester, NY (US); Brian Meyer, Hamlin, NY (US)

(73) Assignee: RC Imaging, Inc., Hilton, NY (US)

( * ) Notice: Subject to any disclaimer, the term of this patent is extended or adjusted under 35 U.S.C. 154(b) by 362 days.

(21) Appl. No.: 14/752,025

(22) Filed: Jun. 26, 2015

(65) Prior Publication Data
US 2016/0374759 A1 Dec. 29, 2016

(51) Int. Cl.
| | |
|---|---|
| *E05C 19/02* | (2006.01) |
| *E05B 65/00* | (2006.01) |
| *A61B 6/00* | (2006.01) |
| *E05B 17/20* | (2006.01) |
| *E05C 19/06* | (2006.01) |
| *A61B 50/00* | (2016.01) |
| *E05C 19/00* | (2006.01) |

(52) U.S. Cl.
CPC .......... *E05B 65/006* (2013.01); *A61B 6/4283* (2013.01); *A61B 50/00* (2016.02); *E05B 17/2034* (2013.01); *E05C 19/06* (2013.01); *Y10T 292/0956* (2015.04); *Y10T 292/1089* (2015.04)

(58) Field of Classification Search
CPC ......... Y10T 292/0911; Y10T 292/0926; Y10T 292/0934; Y10T 292/0956; Y10T 292/1043; Y10T 292/1051; Y10T 292/1089

USPC .............................. 292/70, 78, 106, 207, 302
See application file for complete search history.

(56) References Cited

U.S. PATENT DOCUMENTS

| | | | | |
|---|---|---|---|---|
| 286,935 | A * | 10/1883 | Lee ..................... | E05B 65/0811 292/128 |
| 301,804 | A * | 7/1884 | Chevremont .......... | E05F 11/00 292/207 |
| 480,688 | A * | 8/1892 | Bennett .................. | E05F 11/00 292/207 |

(Continued)

OTHER PUBLICATIONS

DR and CR Protectors, http://www.clearimagedevices.com/files/2012-DR-Panel.pdf, May 6, 2015.

(Continued)

*Primary Examiner* — Carlos Lugo
(74) *Attorney, Agent, or Firm* — Tracy Jong Law Firm; Tracy P. Jong; Cheng Ning Jong (57) ABSTRACT

A lockable retainer assembly adapted for retaining or releasing a panel having at least one edge by preventing or allowing movement of an edge of the panel. The lockable retainer assembly includes a rocker rotatably disposed at the edge, the rocker having a slot and is configured to protrude into the panel's path of movement when the rocker is rotatably disposed in a relaxed position. The rocker is configured to clear the panel's path of movement when the rocker is rotatably disposed in a depressed position. A lock is slidingly disposed within the slot and adapted to prevent rotation of the rocker when the lock is disposed in a relaxed position and allow rotation of the rocker when the lock is disposed in a depressed position. In the depressed position, the clears the path of movement of the panel, enabling the panel to be inserted or removed through the path.

7 Claims, 14 Drawing Sheets

(56) References Cited

U.S. PATENT DOCUMENTS

| | | | | |
|---|---|---|---|---|
| 688,491 A * | 12/1901 | Sigler | A45C 13/06 292/204 |
| 711,696 A * | 10/1902 | Cook | E05B 15/0093 292/106 |
| 719,976 A * | 2/1903 | Zesiger | E05C 19/02 292/207 |
| 1,280,048 A * | 9/1918 | Lavender | E05B 65/46 292/216 |
| 3,087,749 A * | 4/1963 | Capton | E05C 3/24 292/106 |
| 3,571,977 A * | 3/1971 | Abeel | B64C 1/1446 244/129.5 |
| 4,367,971 A * | 1/1983 | Coren | B25B 23/0035 292/128 |
| 4,422,794 A * | 12/1983 | Deken | E21B 17/046 292/128 |
| 4,759,574 A * | 7/1988 | James | E05C 19/145 292/1 |
| 4,993,759 A * | 2/1991 | Thomas | E05C 3/047 292/106 |
| 5,044,810 A * | 9/1991 | Matsuoka | H05K 7/1007 292/128 |
| 5,785,398 A * | 7/1998 | Park | E05C 1/10 292/128 |
| 6,155,616 A * | 12/2000 | Akright | E05B 5/00 292/198 |
| 6,902,137 B2 * | 6/2005 | Brzeski | B64C 1/1407 244/118.5 |
| D656,614 S | 3/2012 | Stinson | |
| 8,162,359 B2 * | 4/2012 | Haruyama | G03G 15/5016 292/194 |
| D683,459 S | 5/2013 | Haltof et al. | |
| 2010/0014225 A1 | 1/2010 | Reina et al. | |

OTHER PUBLICATIONS

Reina Imaging, Model # PDRNGDRX, http://www.zzmedical.com/mobile-dr-panel-holder-for-carestream-drx-1.html, Jun. 26, 2015.

* cited by examiner

LOCKABLE RETAINER ASSEMBLY

BACKGROUND OF THE INVENTION

1. The Field of the Invention

The present invention is directed generally to a lockable retainer assembly. More specifically, the present invention is directed to a radiographic detector protector equipped with a lockable retainer assembly where the contents of the protector are releasable from the protector or re-insertable into the protector using only one hand of a user and the lock of retainer must be depressed simultaneously with the retainer, thereby eliminating false or accidental release of the protector's contents.

2. Background Art

Radiographic detectors are frequently used in medical imaging. Attempts have been made in the past to protect such detectors from impacts due to falls and abuses, undesirable physical contact with peripheral equipment and even loads, e.g., placed upon them by their users. Accidental release of such detectors can also occur especially when locking mechanisms of the protectors are inadvertently de-activated when placed in contact with and dragged over materials such as a bed sheet, pillow, mattress, etc. U.S. Des. Pat. No. D656614 to Stinson (hereinafter Stinson) discloses a digital radiography (DR) imager protector. It appears that Stinson's protector is simply a sleeve-style enclosure having an opening at one longitudinal end for receiving an imager and a briefcase-style carrying handle for ease of transport. Stinson appears to require that the imager to be slid in its entirety through the opening of the enclosure when the imager is being seated or when the imager is being removed from the enclosure. Stinson is silent on whether the imager can be securely held or locked in place while seated in the protector or the means for locking the imager in place while seated in the protector.

U.S. Pat. Pub. No. 20100014225 of Reina et al. (hereinafter Reina) discloses an X-ray grid handler or grid encasement device having built-in handles and a way of positively locking the grid into the encasement device. It was purported that the encasement device can optionally have a spring-loaded trapping and ejection mechanism to hold the grid or imaging medium and free it when desired. Among other shortcomings, Reina fails to disclose an encasement capable of preventing accidental release of its contents. Further, an encasement offered by Reina Imaging, Model # PDRNGDRX featuring a hand-actuated retainer may be prone to accidental actuation of the retainer, causing the contents of the encasement to easily fall out by accident.

A protector offered by Clear Image Devices LLC (hereinafter CID) features an edge having a rectangular profile. As such, if such an edge comes in contact with a hard surface during a fall, the rectangular profile does not cause a rotation to lessen such impact. Further, CID's protector is incapable of guarding against accidental removal of a panel from its protector if the panel is transported while seated in the protector. No locks are provided as it is disposed over a floor placed panel, making it unsuitable for uses other than floor placed applications.

Thus, there is a need for a radiographic detector protector that can be placed on various surfaces while in use without fear that the contents of the protector will be accidentally released. There is also a need for a protector that does not require the entire detector to be inserted through a sleeve or one which is compact and easy to be transported. There is further a need for a radiographic detector protector capable of lessening the effects of an impact during a fall.

SUMMARY OF THE INVENTION

In accordance with the present invention, there is provided a lockable retainer assembly adapted for retaining or releasing a panel having at least one edge by preventing or allowing movement of the at least one edge. The lockable retainer assembly includes:
  (a) a rocker rotatably disposed at a portion of the at least one edge, the rocker having a slot and the rocker is configured to protrude into a path of movement of the panel when the rocker is rotatably disposed in a relaxed position and the rocker is configured to clear the path of movement of the panel when the rocker is rotatably disposed in a depressed position; and
  (b) a lock slidingly disposed within the slot, the lock is adapted to prevent rotation of the rocker when the lock is disposed in a relaxed position and allow rotation of the rocker when the lock is disposed in a depressed position,
whereby when both the lock is slidingly disposed in a depressed position and the retainer is rotatably disposed in a depressed position, the retainer clears the path of movement of the panel, enabling the panel to be inserted or removed through the path of movement of the panel. In one embodiment, the panel is a radiographic detector.

In one embodiment, the at least one edge is disposed adjacent an edge of a frame. In one embodiment, the frame is rectangular. In one embodiment, the frame includes a top edge, a bottom edge, two side edges each connecting one end of the top edge and one end of the bottom edge and a channel disposed on the bottom edge. In one embodiment, at least one of the top edge, the bottom edge, the two side edges further includes a bumper. In one embodiment, the bumper includes a cross-sectional profile having a semi-circular shape.

In one embodiment, the lockable retainer assembly further includes at least one spring for urging the retainer to be disposed in a relaxed position or a depressed position.

In one embodiment, the lockable retainer assembly further includes at least one spring for urging the lock to be disposed in a relaxed position or a depressed position.

An object of the present invention is to provide a radiographic detector protector that does not require the entire detector to be inserted through a sleeve to be seated or removed.

Another object of the present invention is to provide a compact radiographic detector protector that is easy to transport.

Another object of the present invention is to provide a radiographic detector protector that has an unlock function that is coupled with its release function, thereby capable of preventing accidental release of a radiographic detector contained within the protector.

Another object of the present invention is to provide a radiographic detector protector that has combined unlock and release functions that are operable using one hand.

Another object of the present invention is to provide a radiographic detector protector capable of softening the impact of a fall of the protector and the detector or any contents contained therein.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST

2—radiographic detector protector
4—wiring cutout
6—retainer assembly
8—rocker
10—slot
12—opening
14—cavity
16—channel
18—panel or radiographic detector
20—top portion of panel
21—bottom portion of panel
22—pin
24—limit pin
26—spring
27—slot for accommodating lock spring
28—spring
29—slot for accommodating rocking spring
30—slot
32—top edge
34—bottom edge
36—side edge
38—pivot
40—block
42—finger
44—protrusion
46—cavity
48—lock assembly
50—ridge
52—hand
54—direction in which panel is rotated to be removed from or inserted in cavity of protector
56—seat
58—angle at which retainer is disposed, allowing removal or insertion of panel
60—first member or button
62—shield
64—floor
66—handle
68—second member or lever
70—bumper Particular Advantages of the Invention The present radiographic detector protector includes an unlock function that is coupled with its release function, thereby capable of preventing accidental release of a radiographic detector contained within the protector. The unlock function is implemented with a lock which must be depressed before a retainer which is coupled to the lock, can be disposed in a position to allow a radiographic detector contained within the protector to be released. The lock and retainer are adapted to be disposed in a depressed position with only one hand. In disposing the lock and retainer in such a position, the lock is first depressed with one or more fingers of a hand followed by the depression of the retainer with one or more fingers of the same hand to move the retainer out of the way of the path in which the radiographic detector can be removed from the protector or inserted in the protector.

The present radiographic detector protector is capable of softening the impact of a fall of the protector and the detector contained therein.

Detailed Description of a Preferred Embodiment

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "radiographic detector" or "detector" is used herein to mean a radiation cassette, imaging grid, device, panel, board or structure having a generally rectangular shape definable using a set of dimensions, e.g., length, width and height.

Figure 1:
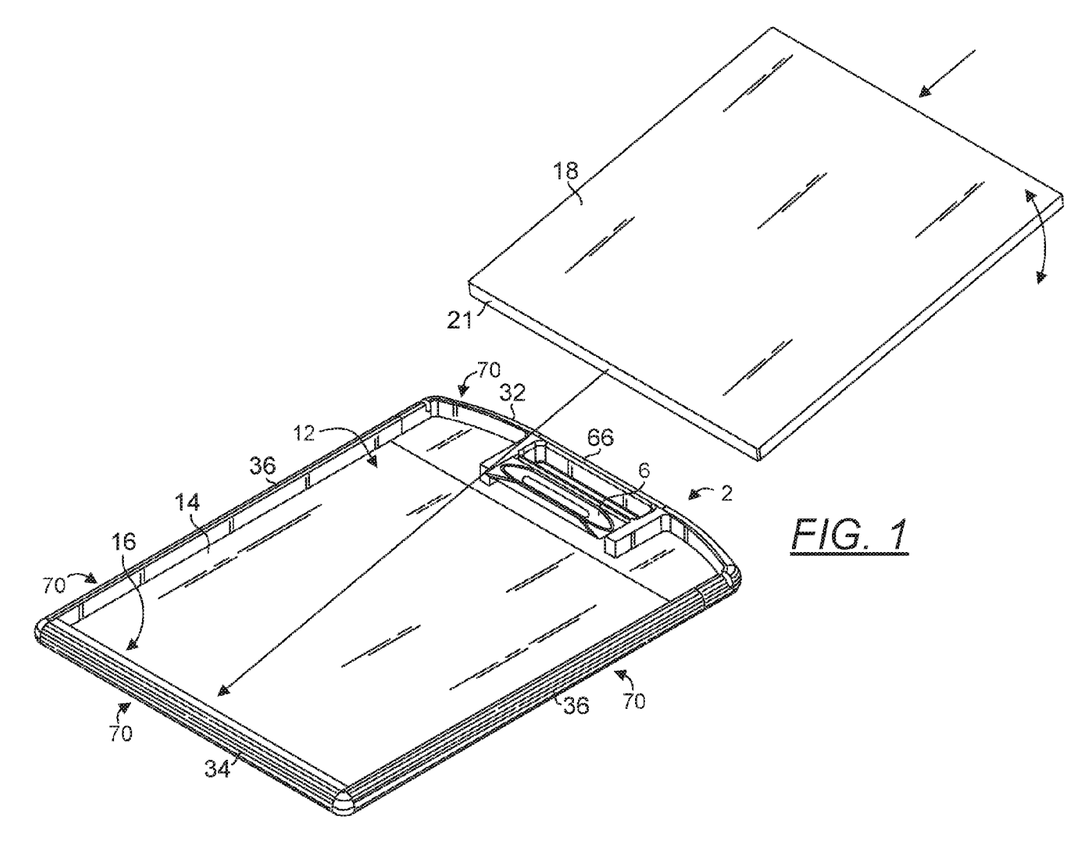
FIG. 1 is a top rear perspective view of one embodiment of the present protector, depicting a panel being aligned to be inserted in the protector's cavity.
Figure 2:
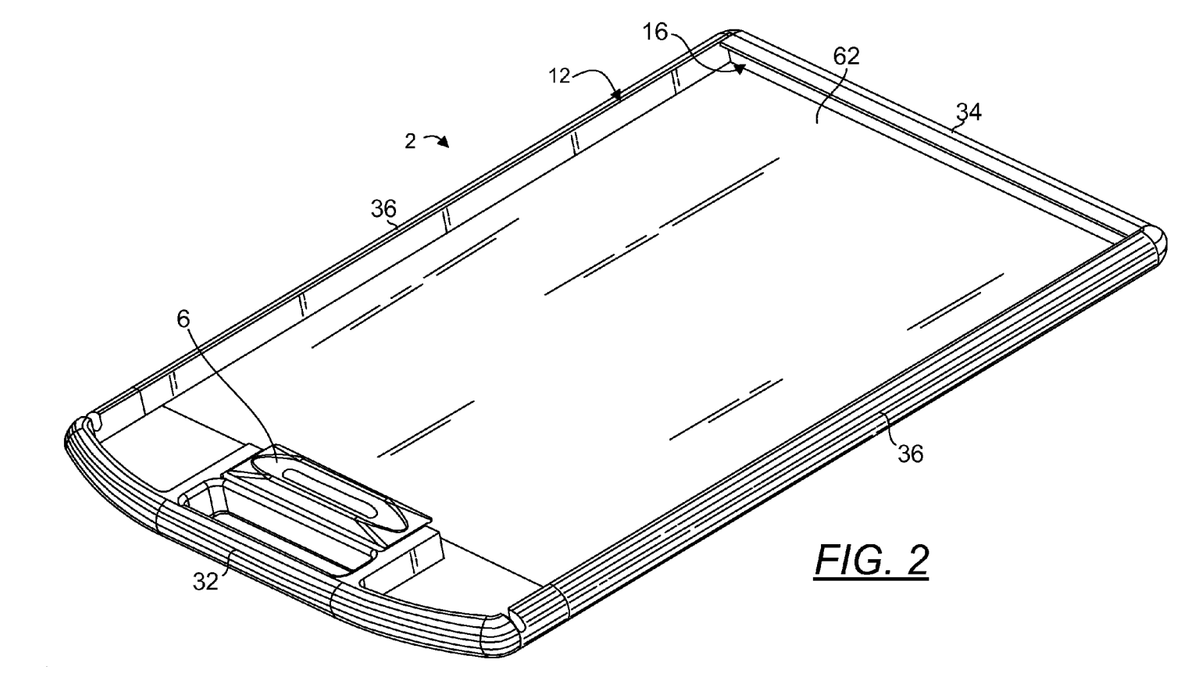
FIG. 2 is a top front perspective view of one embodiment of the present protector.
Figure 3:
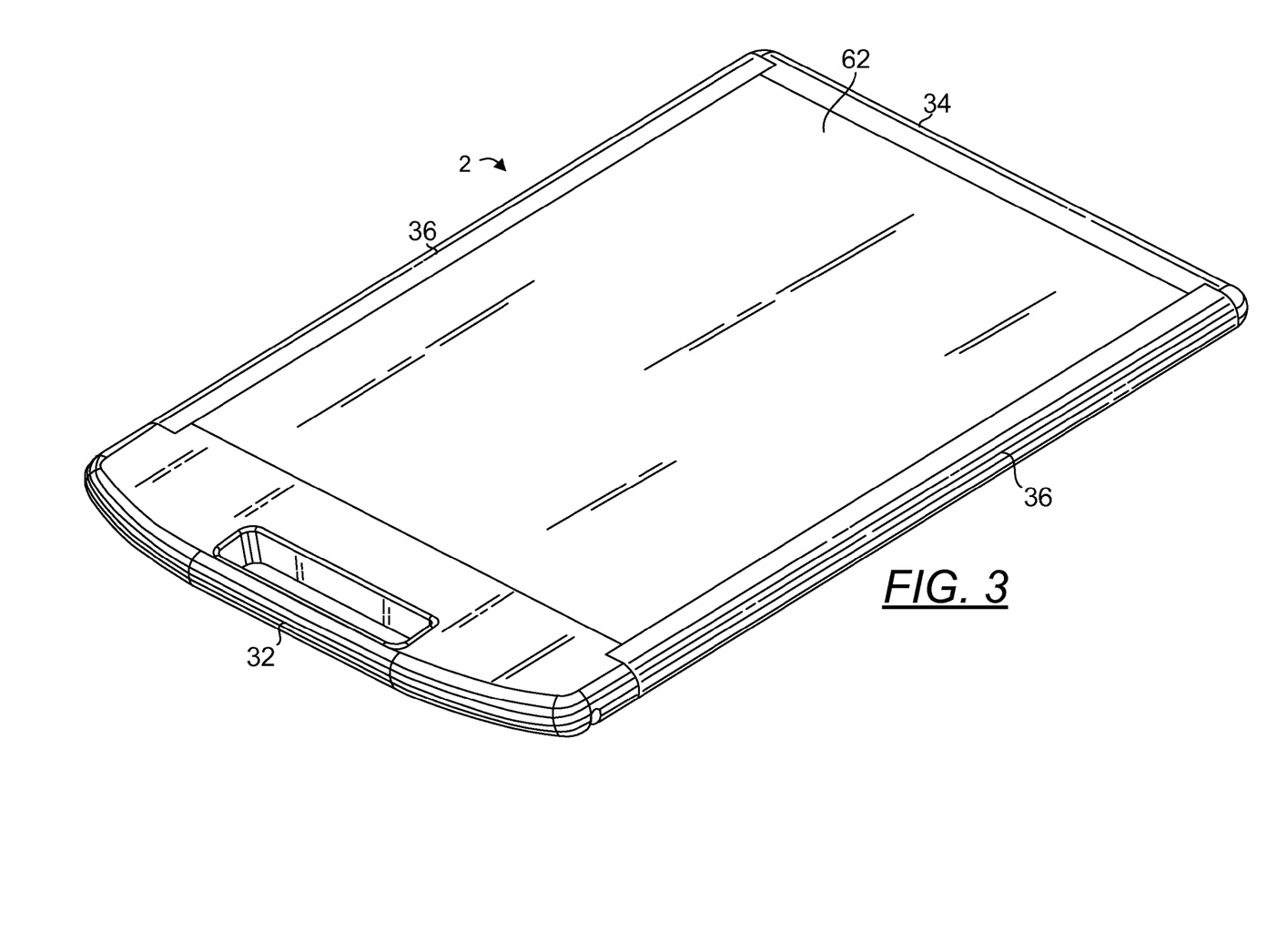
FIG. 3 is a bottom front perspective view of one embodiment of the present protector.
Figure 4:
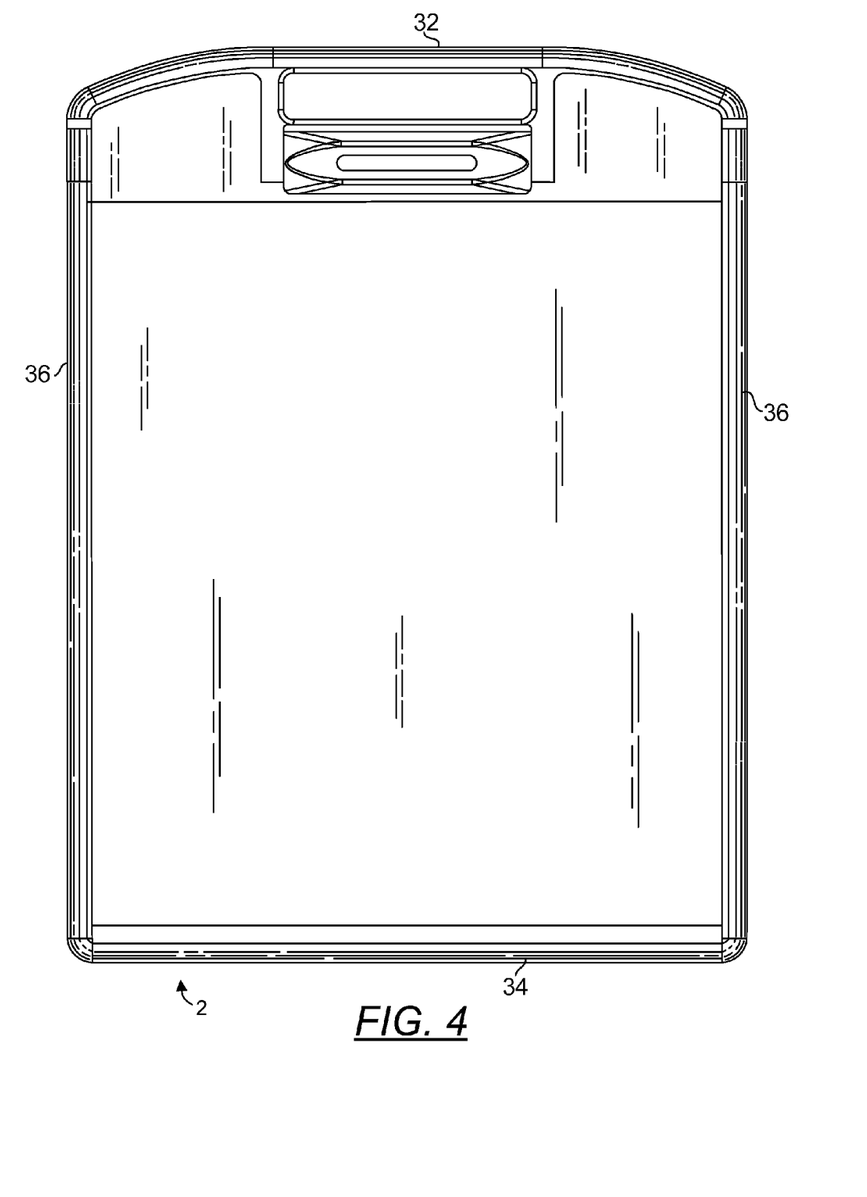
FIG. 4 is a top view of one embodiment of the present protector.
Figure 5:
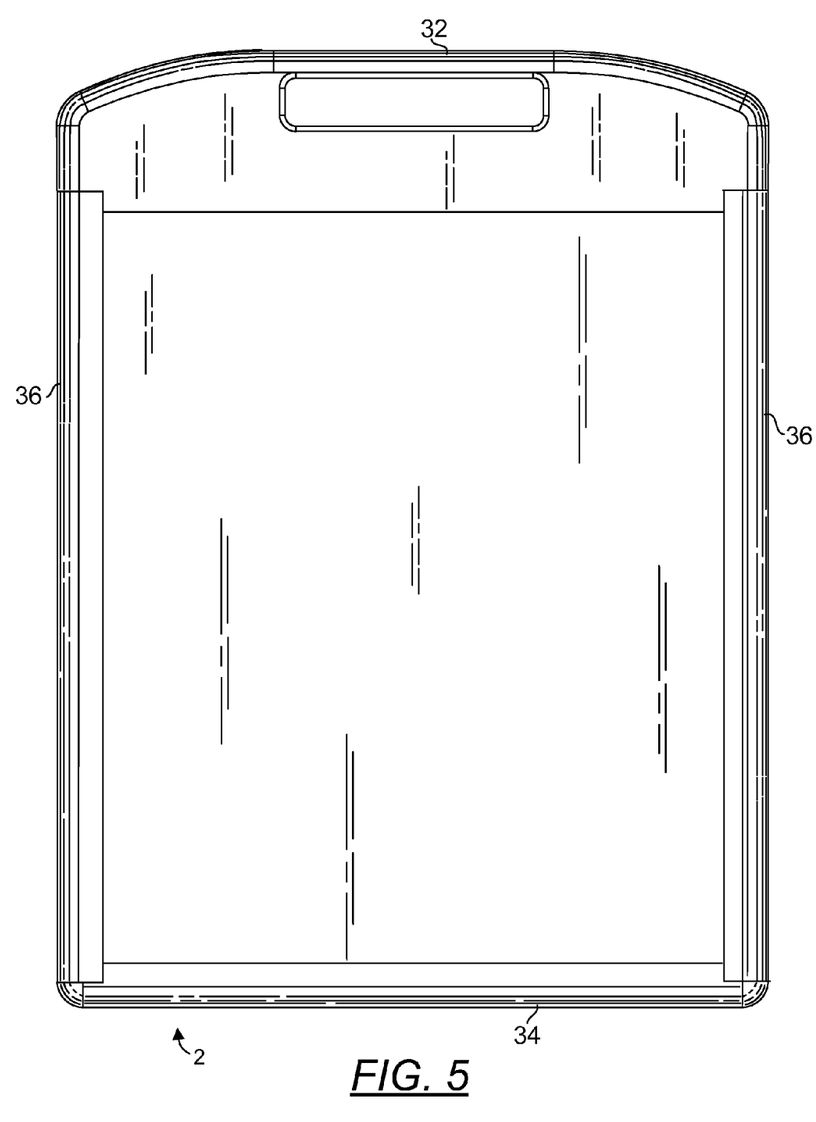
FIG. 5 is a bottom view of one embodiment of the present protector.
Figure 6:
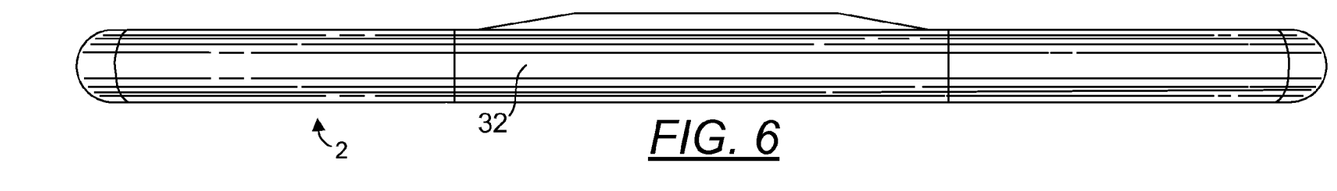
FIG. 6 is a front view of one embodiment of the present protector.
Figure 7:
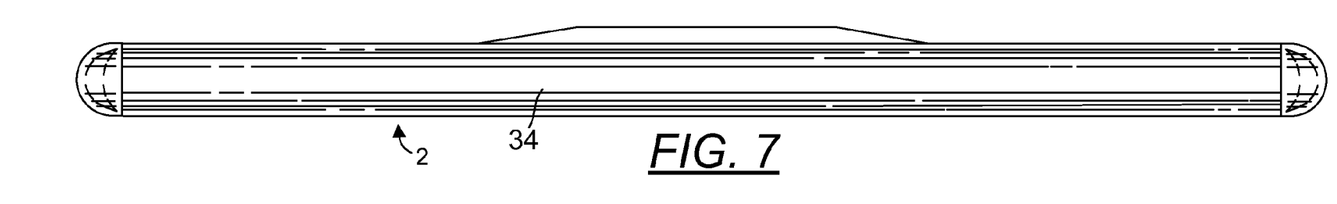
FIG. 7 is a rear view of one embodiment of the present protector.
Figure 10:
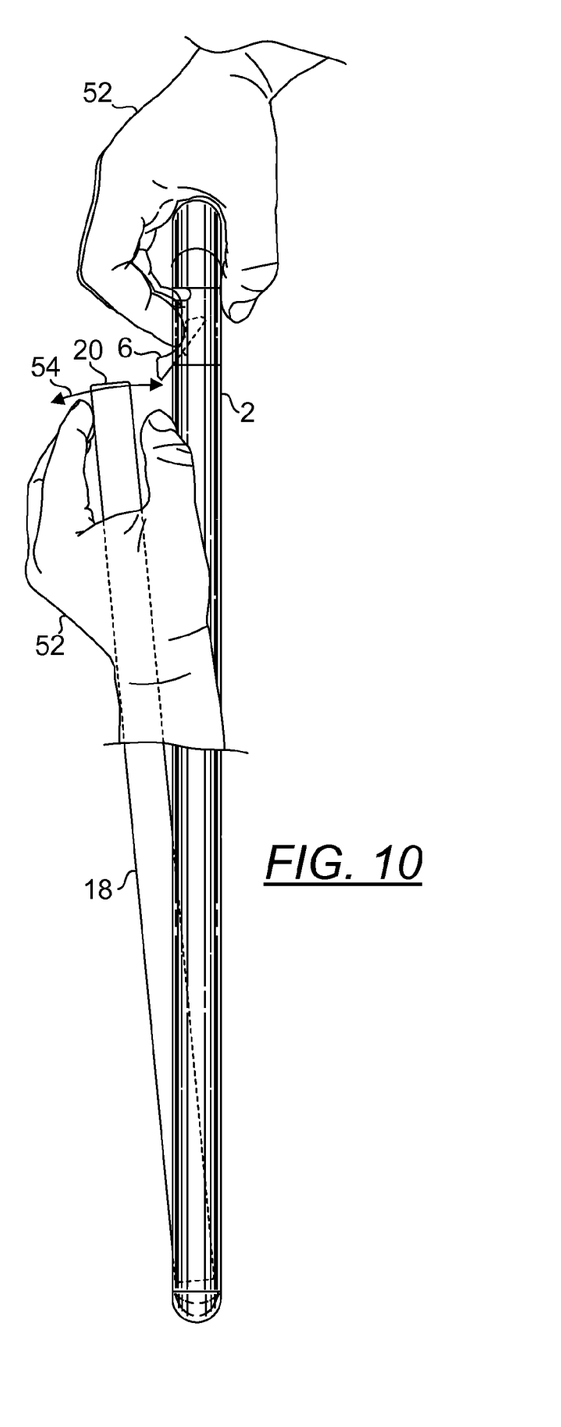
FIG. 10 is a side view of one embodiment of the present protector, depicting a panel being removed from or inserted in the protector's cavity.

FIG. 1 is a top rear perspective view of one embodiment of the present protector 2, depicting a panel 18 being aligned to be inserted in the protector's cavity 14 via opening 12. FIG. 2 is a top front perspective view of one embodiment of the present protector 2, revealing a channel 16 disposed on the bottom edge of the protector 2. FIG. 3, 4, 5, 6, 7 is a bottom front perspective, top, bottom, front, rear view of one embodiment of the present protector 2, respectively. FIG. 10 is a side view of one embodiment of the present protector, depicting a panel being removed from or inserted in the protector's cavity 14.

In one example, a radiographic detector or panel 18 measures about 18⅛ inch in length, about 15⅛ inch in width and about ⅝ inch in height. In installing the panel 18 in the cavity 14, the panel 18 is first orientated such that its bottom portion is aligned with channel 16. The panel 18 is then moved towards the cavity 14 until the bottom portion 21 of the panel 18 is seated in the channel 16. The retainer assembly 6 is then disposed in a depressed position as shown in FIG. 10 such that the top edge 20 of the panel 18 can clear the retainer assembly 6 and the panel 18 can be seated in or removed from the cavity 14 in direction 54.

Figure 8:
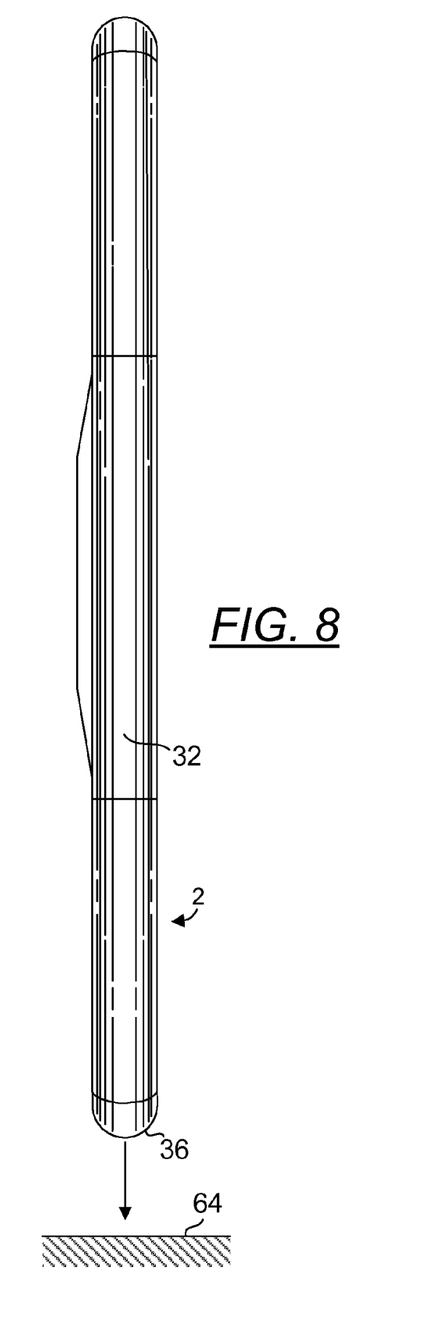
FIG. 8 is a front view of one embodiment of the present protector, depicting the protector just before impact on a floor.
Figure 9:
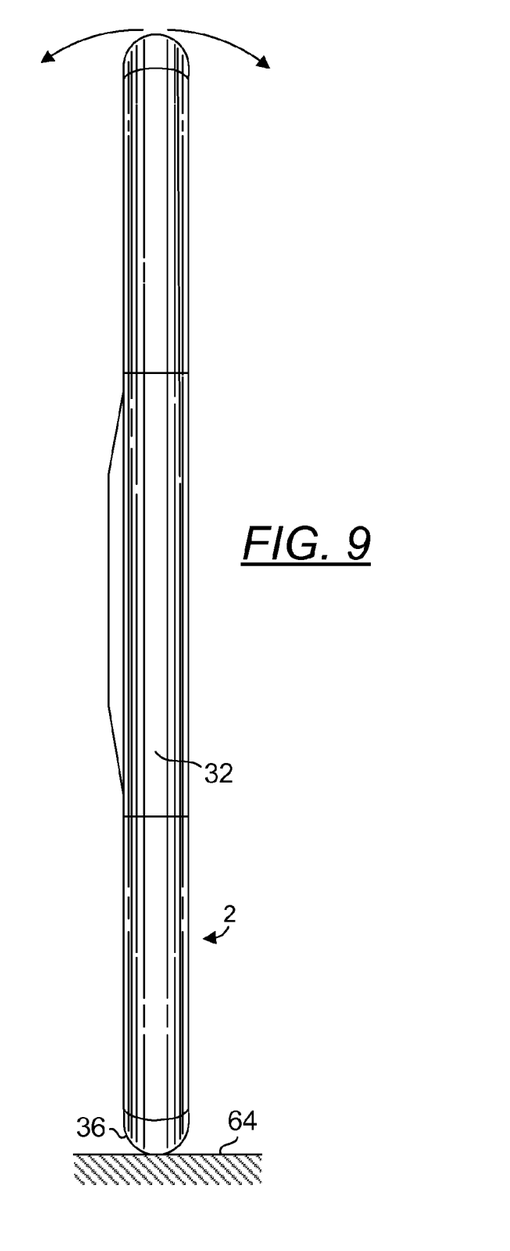
FIG. 9 is a front view of one embodiment of the present protector, depicting the protector at impact on a floor.

The protector 2 is essentially a frame including a top edge 32, a bottom edge 34, two side edges 36 each connecting one end of the top edge 32 and one end of the bottom edge 34, a channel 16 disposed on the bottom edge 34 and a shield 62 disposed on the rear face of the frame, providing a barrier and structural integrity to the frame. Each edge 32, 34, 36 further includes a bumper 70. In one embodiment, the frame is rectangular and configured to receive a rectangularly-shaped panel. In one embodiment, the bumper includes a cross-sectional profile having a semi-circular shape. FIGS. 8 and 9 depict the manner in which such profile can aid in deflecting impacts imparted to the protector 2 or its contents. FIG. 8 is a front view of one embodiment of the present protector, depicting the protector just before impact on a floor 64. FIG. 9 is a front view of one embodiment of the present protector, depicting the protector at impact on a floor 64. When configured in this shape, the edge 36 coming in contact with the floor 64 causes rotation of the frame in one of directions depicted so as to lessen the shock experienced in the frame and hence the contents carried within the frame.

In the ensuing disclosure on the present lockable retainer assembly, it shall be kept in mind that the assembly works by preventing or allowing movement of the panel at one of its edges. The lockable retainer assembly includes a retainer assembly 6 and a lock assembly 48. While seated in the cavity 14, the bottom end of the detector 18 is secured in channel 16 and the top end of the detector 18 is secured using the combined lock and retainer assemblies. The retainer assembly 6 includes a retainer having a rocker 8 pivotably connected about a pivot 22 disposed at a portion of the top edge. The rocker 8 is essentially a block having a top surface configured to be engaged with a user's hand 52, side surfaces having features for receiving pins or pivots 22 and interacting with pins 24 and a slot 10 for receiving the button 60. A briefcase-type handle 66 is disposed at a portion of the top edge to facilitate carrying of the protector 2. The rocker 8 includes a slot 10 and the rocker 8 is configured to protrude into a path of movement of the panel 18 when the rocker 8 is rotatably disposed in a relaxed position. The rocker 8 is configured to clear the path of movement of the panel 18 when the rocker 8 is rotatably disposed in a depressed position.

Figure 11:
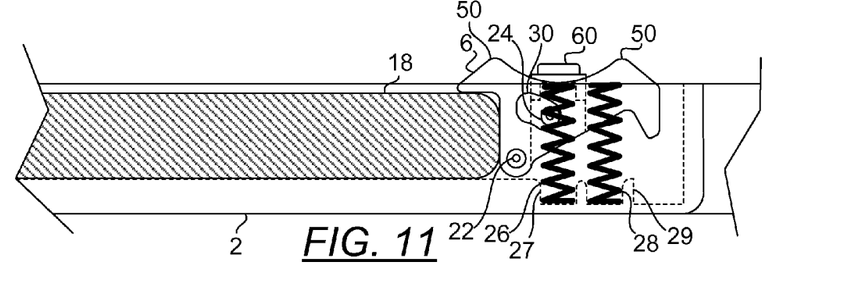
FIG. 11 is a partial side partially transparent view of one embodiment of the present protector, depicting the springs used in the lock and retainer assemblies.
Figure 12:
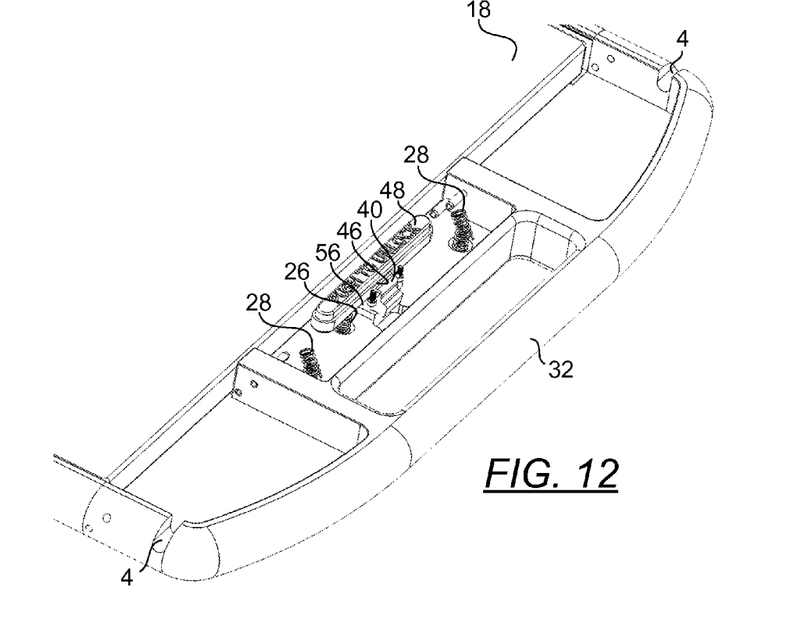
FIG. 12 is a partial top front perspective view of one embodiment of the present protector, depicting internal components of the lock and retainer assemblies.
Figure 13:
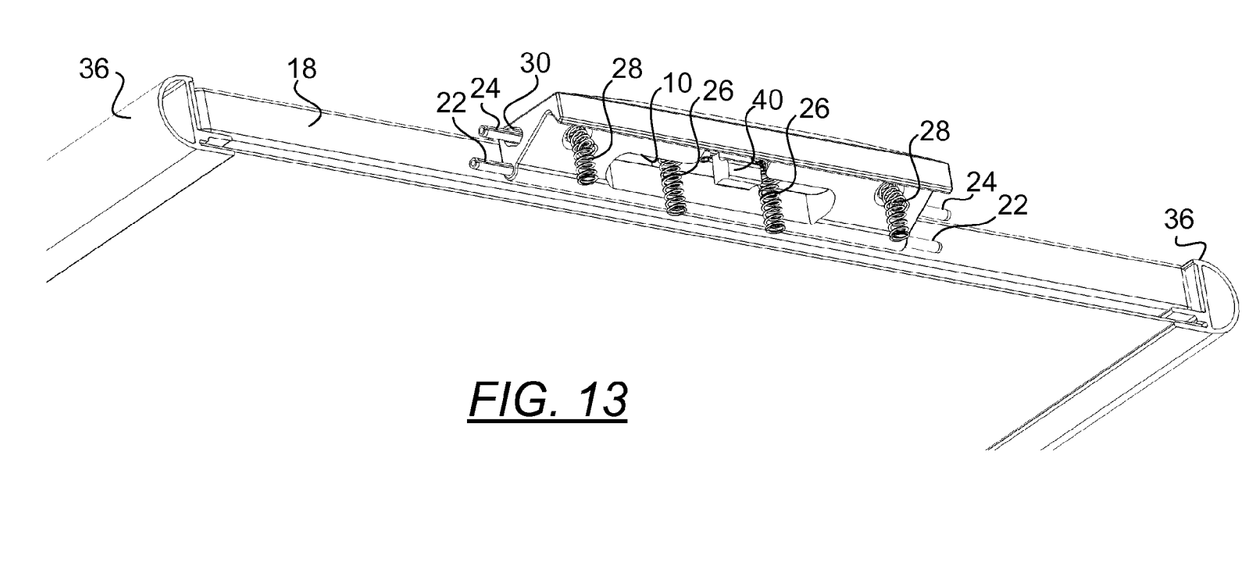
FIG. 13 is a partial bottom front perspective view of one embodiment of the present protector, depicting internal components of the lock and retainer assemblies.
Figure 14:
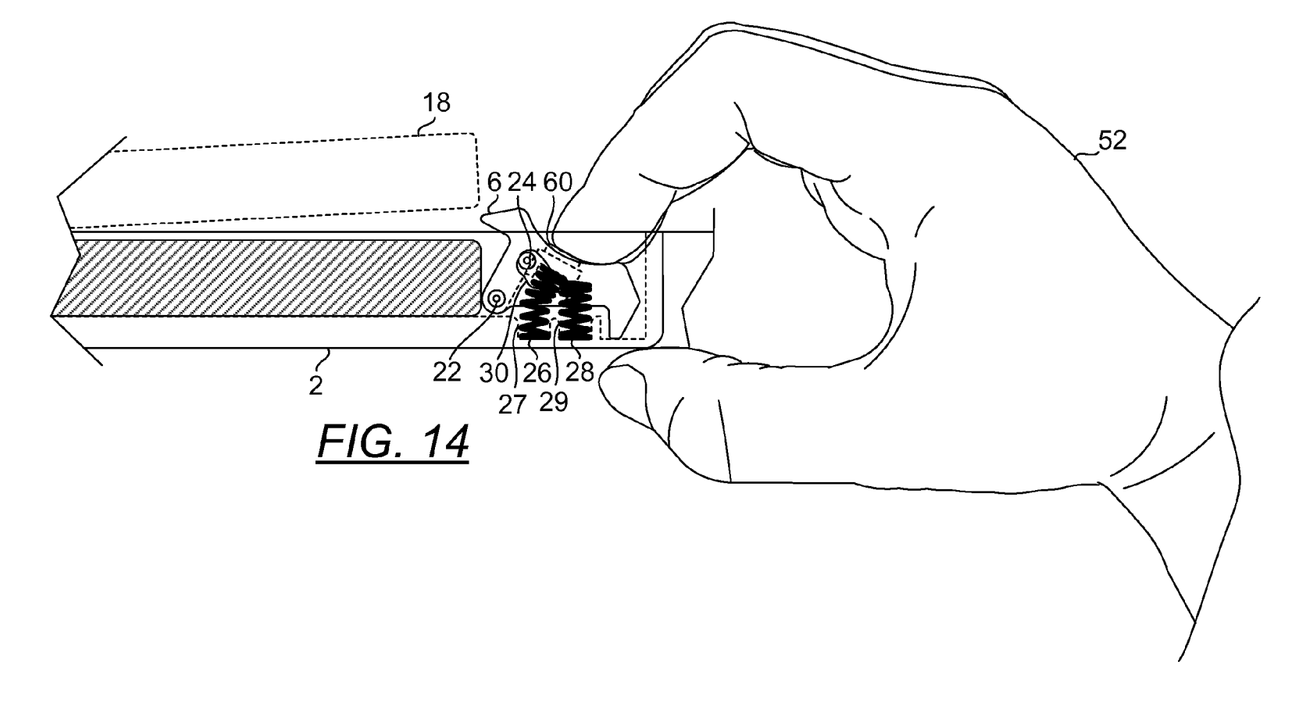
FIG. 14 is a partial side partially transparent view of one embodiment of the present protector, depicting the springs used in the lock and retainer assemblies when the lock and retainer are being depressed.
Figure 15:
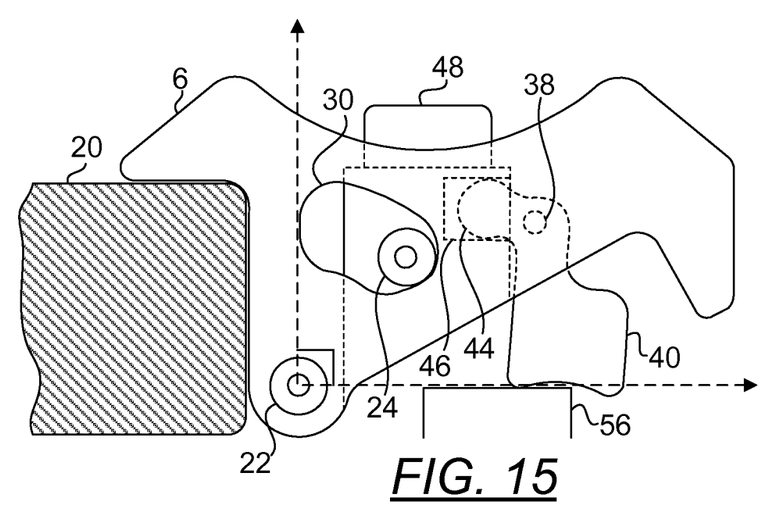
FIG. 15 is a partial side partially transparent view of one embodiment of the present protector, depicting the interactions between the lock and retainer assemblies.
Figure 16:
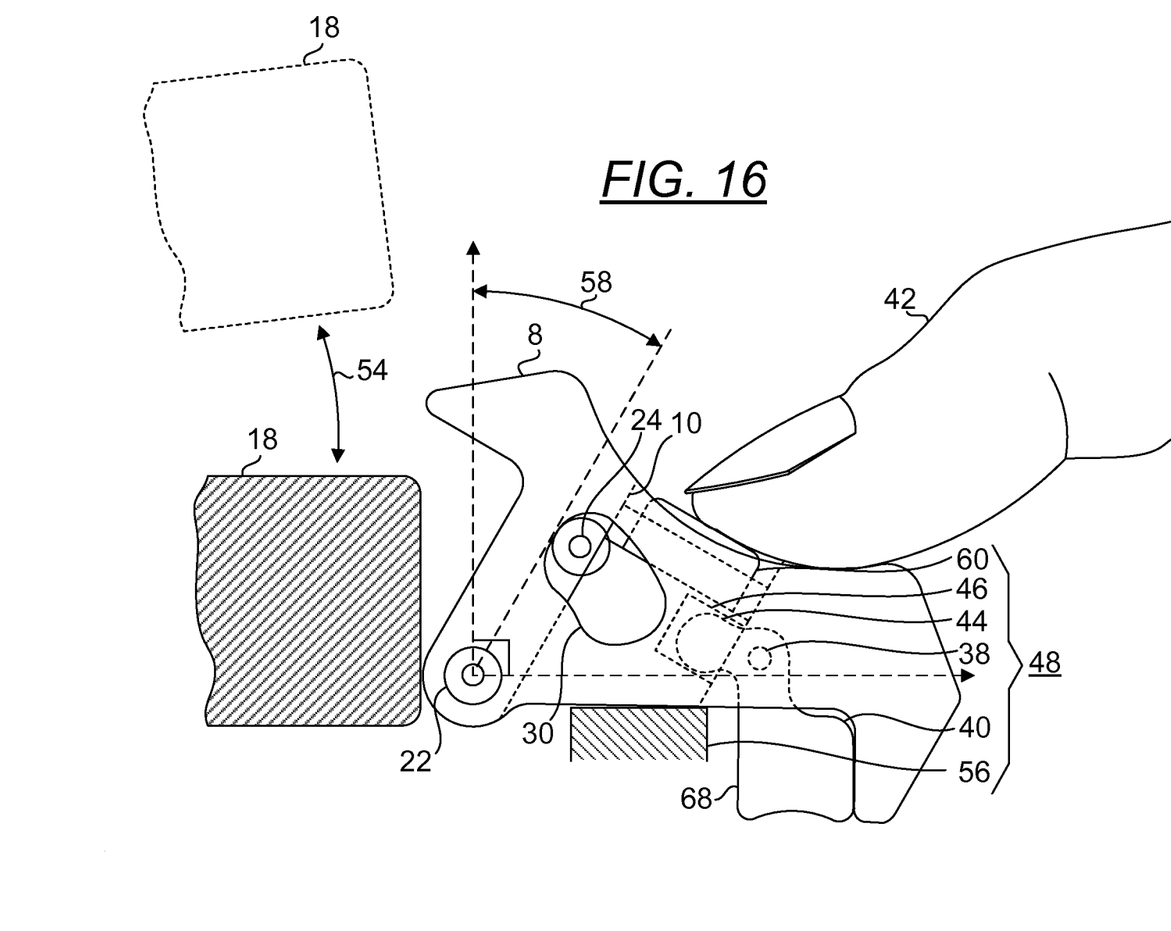
FIG. 16 is a partial side partially transparent view of one embodiment of the present protector, depicting the interactions between the lock and retainer assemblies when the button and rocker are being depressed.

FIG. 11 is a partial side partially transparent view of one embodiment of the present protector 2, depicting the springs used in the lock and retainer assemblies 48, 6. FIG. 12 is a partial top front perspective view of one embodiment of the present protector 2, depicting internal components of the lock and retainer assemblies 48, 6 with the rocker 8 of the retainer assembly 6 removed. FIG. 13 is a partial bottom front perspective view of one embodiment of the present protector, depicting internal components of the lock and retainer assemblies 48, 6 with the top edge 32 and a portion of the shield 62 removed to reveal the rocker 8 and its spatial relationship with the springs 26, 28. FIG. 14 is a partial side partially transparent view of one embodiment of the present protector, depicting the springs 26, 28 used in the lock and retainer when the lock and retainer are being depressed. FIG. 15 is a partial side partially transparent view of one embodiment of the present protector, depicting the interactions between the lock and retainer assemblies 48, 6. FIG. 16 is a partial side partially transparent view of one embodiment of the present protector, depicting the interactions between the lock and retainer assemblies 48, 6 when the button 60 and rocker 8 are being depressed. The lock assembly 48 includes a button 60, a seat 56 and a lever 68. The button 60 is configured to travel in a path within the slot 10, the button 60 having a cavity 46 disposed on one of its side walls. The lever 68 is pivotably connected to the rocker 8 at a pivot 38, the lever 68 having a protrusion 44 disposed about the pivot 38 of the lever 68 on a first end of the lever 68 and a block 40 disposed about the pivot 38 of the lever 68 on a second end of the lever 68. The protrusion 44 is configured to be disposed within the cavity 46. When the button 60 is urged against the lever 68, the lever 68 is rotated about the pivot 38 of the lever 68 to clear the seat 56, allowing the retainer to be disposed in the depressed position of the retainer at an angle 58 to allow movement of the top edge 20 of the panel 18. When the button 60 is relieved from urging against the lever 68, the lever 68 is disposed in a position to be seated on the seat 56 to return the retainer to the relaxed position of the retainer and prevent movement of the top edge 20 of the panel 18. Therefore, in order for the panel 18 to be released while it is seated in the cavity 14, the button 60 must be depressed simultaneously with the rocker 8. Further, the button 60 must be depressed in a direction not parallel to the direction in which the protector 2 can normally be accidentally dragged on a surface, dramatically reducing any opportunities of accidental release of panel 18 contained within the cavity 14.

It shall be noted that two springs 28 are seated in their respective slots 29 to urge against the rocker 8 to dispose it in the relaxed position or the depressed position. Left untouched, the rocker 8 is disposed in the relaxed position as shown in FIG. 11 with the springs 28 still exerting a force to dispose the rocker 8 in a position ready to be depressed again. The limit pin 24 which is disposed within slot 30 limits the rotation of rocker 8 about pin or pivot 22 such that when disposed in the relaxed position, the surface of rocker 8 includes features which aid a user in engaging the rocker 8. It shall be noted that in the cross-sectional profile of the rocker 8 shown in FIG. 14 that ridges 50 are featured on the top surface of the rocker 8 to aid a user in engaging the rocker 8 while holding down button 60. Two springs 26 are seated in their respective slots 27 to urge against the button 60 in the path to dispose the button 60 in a relaxed position or a depressed position. Alternatively, although less desirably, each set of springs 26, 28 may be replaced with a single spring.

Figure 17:
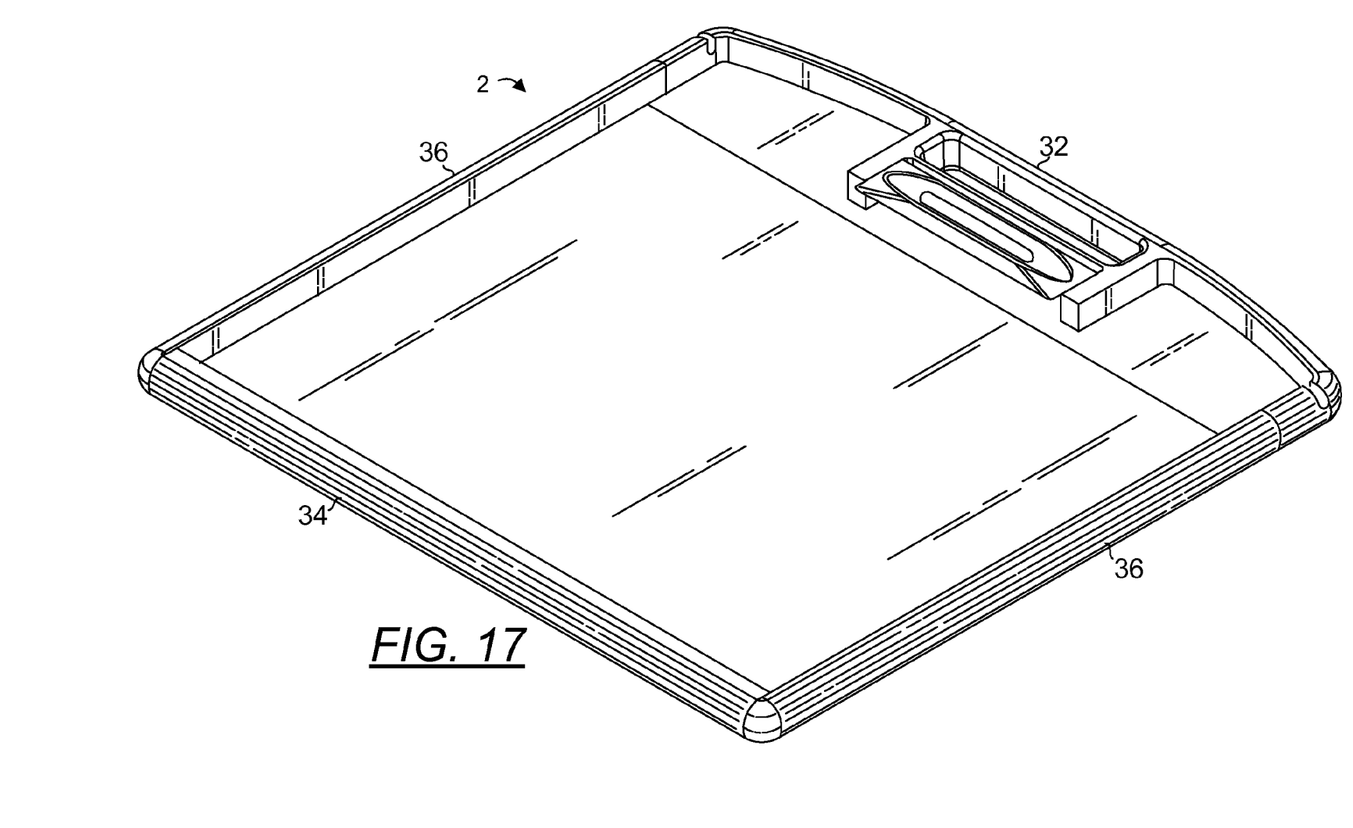
FIG. 17 is a top rear perspective view of another embodiment of the present protector.

FIG. 17 is a top rear perspective view of another embodiment of the present protector 2. It shall be noted that the handle 66 of protector 2 shown in FIGS. 1-7 is disposed on one edge along the width of the protector 2. It is conceivable that a handle 66 be disposed on one edge along the length of the protector 2 as shown in FIG. 17. Further, wiring cutouts 4 are shown disposed along a side edge of the protector's frame to securely hold any electrical or data cables going into a panel 18 while it is seated in the cavity 14 or any cables emanating from the panel 18. Additional cutouts 4 may also be disposed along the top edge of the frame.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which the embodiments should be determined with reference to the appended claims, along with the full scope of equivalents to which such claims are entitled.

What is claimed herein is:

1. A lockable retainer assembly adapted for retaining or releasing a panel having an edge by preventing or allowing movement of the edge, said lockable retainer assembly comprises:
   (a) a retainer assembly comprising:
      (i) a retainer having a rocker pivotably connected about a pivot disposed at a portion of the edge, said rocker having a slot and said rocker is configured to protrude into a path of movement of the panel when said rocker is rotatably disposed in a relaxed position and said rocker is configured to clear said path of movement of the panel when said rocker is rotatably disposed in a depressed position; and
      (ii) at least one spring configured to urge against said rocker to dispose said rocker in one of said relaxed position of said rocker and said depressed position of said rocker; and
   (b) a lock assembly comprising:
      (i) a button configured to travel in a path within said slot, said button having a cavity;
      (ii) at least one spring configured to urge against said button in said path to dispose said button in one of a relaxed position and a depressed position;
      (iii) a seat; and
      (iv) a lever pivotably connected to said rocker at a pivot, said lever having a protrusion disposed about said pivot of said lever on a first end of said lever and a block disposed about said pivot of said lever on a second end of said second member, wherein said protrusion is configured to be disposed within said cavity, whereby when said button is urged against said second member, said lever is rotated about said pivot of said lever to clear said seat and allowing said retainer to be disposed in said depressed position of said retainer to allow movement of the at least one edge and when said button is relieved from urging against said second member, said lever is disposed in a position to be seated on said seat to return said retainer to said relaxed position of the retainer and prevent movement of the at least one edge.

2. The lockable retainer assembly of claim 1, wherein the edge is disposed adjacent an edge of a frame.

3. The lockable retainer assembly of claim 2, wherein said frame comprises a top edge, a bottom edge, two side edges each connecting one end of said top edge and one end of said bottom edge and a channel disposed on said bottom edge.

4. The lockable retainer assembly of claim 3, wherein at least one of said top edge, said bottom edge, said two side edges further comprises a bumper.

5. The lockable retainer assembly of claim 4, wherein said bumper comprises a cross-sectional profile having a semicircular shape.

6. The lockable retainer assembly of claim 2, wherein said frame is rectangular.

7. The lockable retainer assembly of claim 1, wherein the panel is a radiographic detector.

* * * * *